United States Patent [19]

Jones

[11] 4,320,415
[45] Mar. 16, 1982

[54] METHOD OF AND APPARATUS FOR MEASURING ELECTROPHORETIC MOBILITY OF CELLS

[75] Inventor: Robin Jones, Malvern Link, England

[73] Assignee: National Research Development Corporation, London, England

[21] Appl. No.: 156,798

[22] Filed: Jun. 5, 1980

[30] Foreign Application Priority Data

Jun. 14, 1979 [GB] United Kingdom ............... 20672/79

[51] Int. Cl.³ ............................................. H04N 7/18
[52] U.S. Cl. .................................... 358/105; 358/107; 364/515; 364/555
[58] Field of Search ................ 358/105, 107; 364/515, 364/555

[56] References Cited

U.S. PATENT DOCUMENTS

| | | | |
|---|---|---|---|
| Re. 28,940 | 8/1976 | Komline | 358/105 |
| 3,868,498 | 2/1975 | Guggenbühl | 364/555 |
| 4,025,718 | 5/1977 | Paretti | 358/105 |
| 4,168,510 | 9/1979 | Kaiser | 358/105 |
| 4,179,704 | 12/1979 | Moore | 358/105 |
| 4,218,703 | 8/1980 | Netravali | 358/105 |

OTHER PUBLICATIONS

*Lancet,* Dec. 26, 1970, Field et al., "Lymphocyte Sensitisation: An In-Vitro Test For Cancer?", pp. 1337–1341.

*Primary Examiner*—Howard Britton
*Attorney, Agent, or Firm*—Cushman, Darby & Cushman

[57] ABSTRACT

The electrophoretic mobility of cells in a solution is measured by applying an electric potential along a cell. A linescan camera forms an image frame by line scanning the cell in a direction perpendicular to the cell movement. Two such image frames are correlated to determine cell mobility in the interval between the two frames. Each line scanned is processed to indicate detected cells and a digital number obtained. A frame is thus represented by a series of numbers which may be correlated. Alternatively and more simply each line is scanned and the presence of any detected cell represented by a logic ONE so that an image frame is represented by a series of logic ONES and ZEROS for correlation with a later series. Integration of successive mobility measurements improves the observed results. A tag inserter provides a visible mark on a television screen to indicate cells that are detected.

6 Claims, 8 Drawing Figures

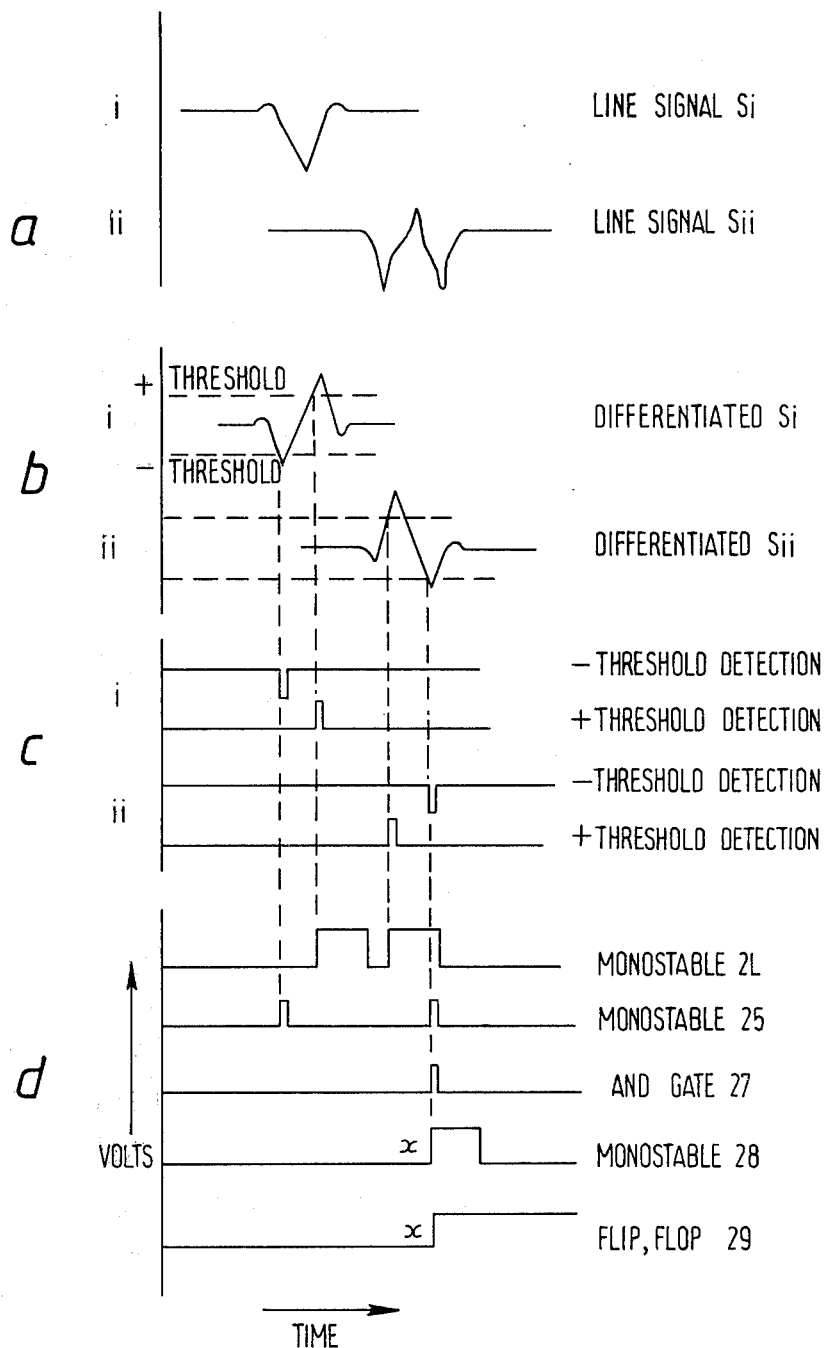

METHOD OF AND APPARATUS FOR MEASURING ELECTROPHORETIC MOBILITY OF CELLS

The invention concerns a method and apparatus for measuring electrophoretic mobility of cells.

One test for the detection of malignant disease is termed the macrophage electrophoretic mobility test (MEM) and is reported in the literature e.g. Field & Caspary, Lancet ii 1337 (1970), British Medical Journal ii 613 (1971); Pritchard et al, Lancet ii 627 (1972), British Journal of Cancer 27.1 (1973).

Electrophoretic mobility is determined by measuring the time taken for a selected cell in a solution (e.g. KC1) to cross two lines a known and fixed distance apart under the influence of a potential difference between two electrodes in the solution. The progress of the cell is observed through a microscope alone or by means of a TV camera and monitor; cells in focus in the stationary layer are chosen at random for measurement and the potential difference is usually reversed for half the measurements to remove direction of migration effects. The timings are affected by an operator who starts and stops a clock. The average of as many timing pairs (one in each direction of movement) as possible are averaged by the formula $$100 \left( \frac{T_2 - T_1}{T_1} \right) = \%$$

slowing where $T_1$ is the average time for a sample without addition and $T_2$ is the average time for a sample with the addition of antigen.

The manual determination of mobility is tedious and error prone through operator fatigue.

One method of measuring the velocity of particles in a fluid automatically is to use laser doppler velocimetry in which doppler shift of laser radiation reflected from moving particles is measured to indicate particle velocity. Unfortunately this technique is expensive and satisfactory results are difficult to achieve.

According to this invention a method of measuring electrophoretic mobility of cells comprises the steps of applying an electric potential to a solution in an electrophoretic chamber, scanning a portion of the chamber in a line by line manner to provide a first image frame, scanning to provide a second image frame a time $\tau$ later, cross correlating the two image frames to determine the image movement in the time $\tau$ and hence the cell mobility of a plurality of cells in the solution.

According to this invention apparatus for measuring electrophoretic mobility of cells comprises an electrophoretic chamber having two spaced electrodes for applying an electric potential to a solution containing cells and separated from the electrodes by membranes, a linescan camera for producing signals representing image frames of the cells within the solution, and a correlator for cross correlating signals representing time spaced image frames to provide average cell mobility.

In one form of correlator each line scanned is processed to indicate the number of detected cells along that line and a digital number produced. One image frame is then represented by a series of digital numbers. Two or more of such series are cross correlated to provide the image shift.

In a more simplified version each line scanned is processed to show whether or not one cell is detected and a single logic one pulse provided for each line. No detected cells result in a logic zero being produced. Thus one image frame is represented by a series of logic ones and zeros. Two such series are cross correlated to provide the image shift.

The invention will now be described by way of example only with reference to the accompanying drawings of which:

FIG. 4 are waveform diagrams of voltage against time;

Figure 5A:
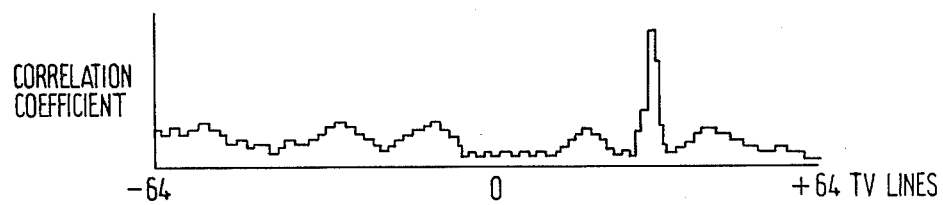
Figure 5B:
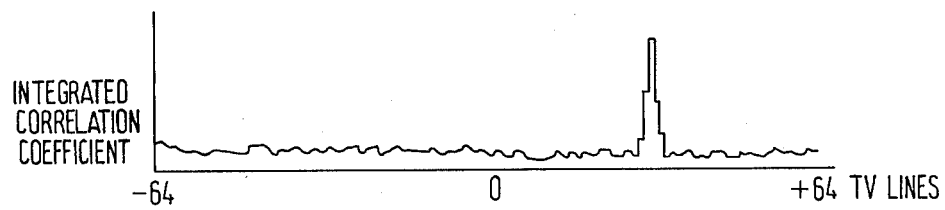
Figure 5C:
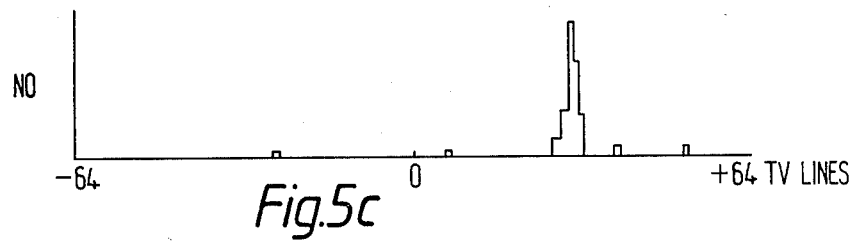
Figure 6:
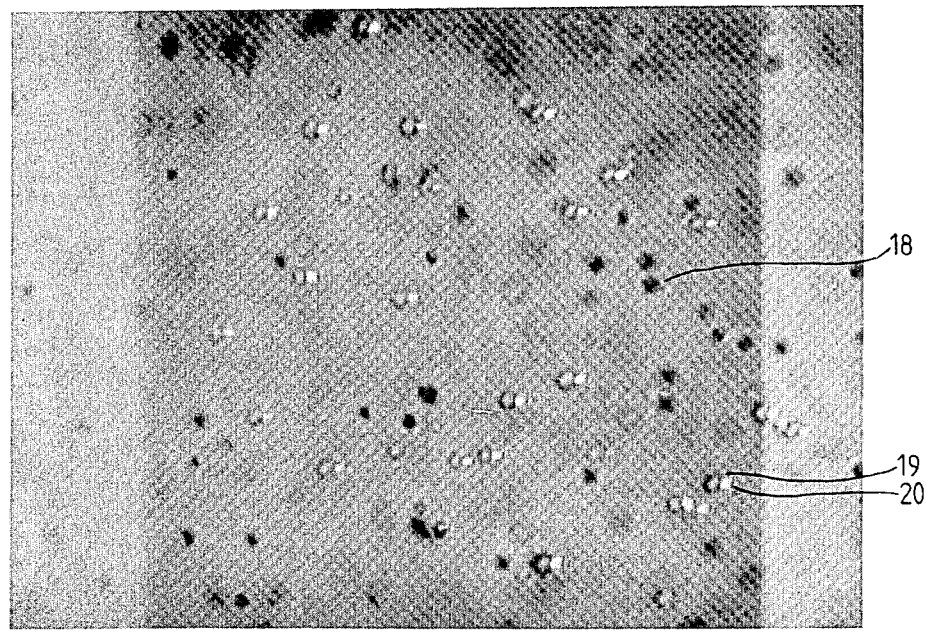

FIGS. 5a and b are correlation and integrated correlation functions against video line time;

FIG. 5c is a graph of probability density function of image movement;

FIG. 6 is a view of cells within a chamber as seen on a video monitor.

Figure 1:
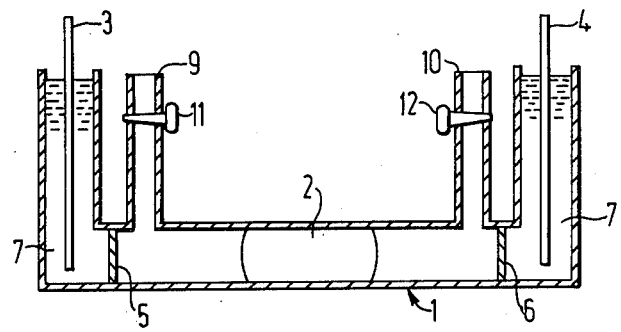
FIG. 1 is a view of an electrophoretic chamber.
Figure 2:
FIG. 2 is a cross section of part of the chamber of FIG. 1.

As seen in FIGS. 1, 2 an electrophoretic apparatus comprises a glass chamber 1 having a flat sided centre portion 2, two electrodes 3, 4 at both ends and two membranes 5, 6 separating the electrodes, immersed in a saline solution 7, from the sample 8 of blood cells in solution (e.g. KC1). A sample 8 is passed into the chamber 1 through pipes 9, 10 controlled by taps 11, 12.

When an electric potential is applied between the electrodes 3, 4 cells migrate from one end of the chamber 1 to the other.

Figure 3:
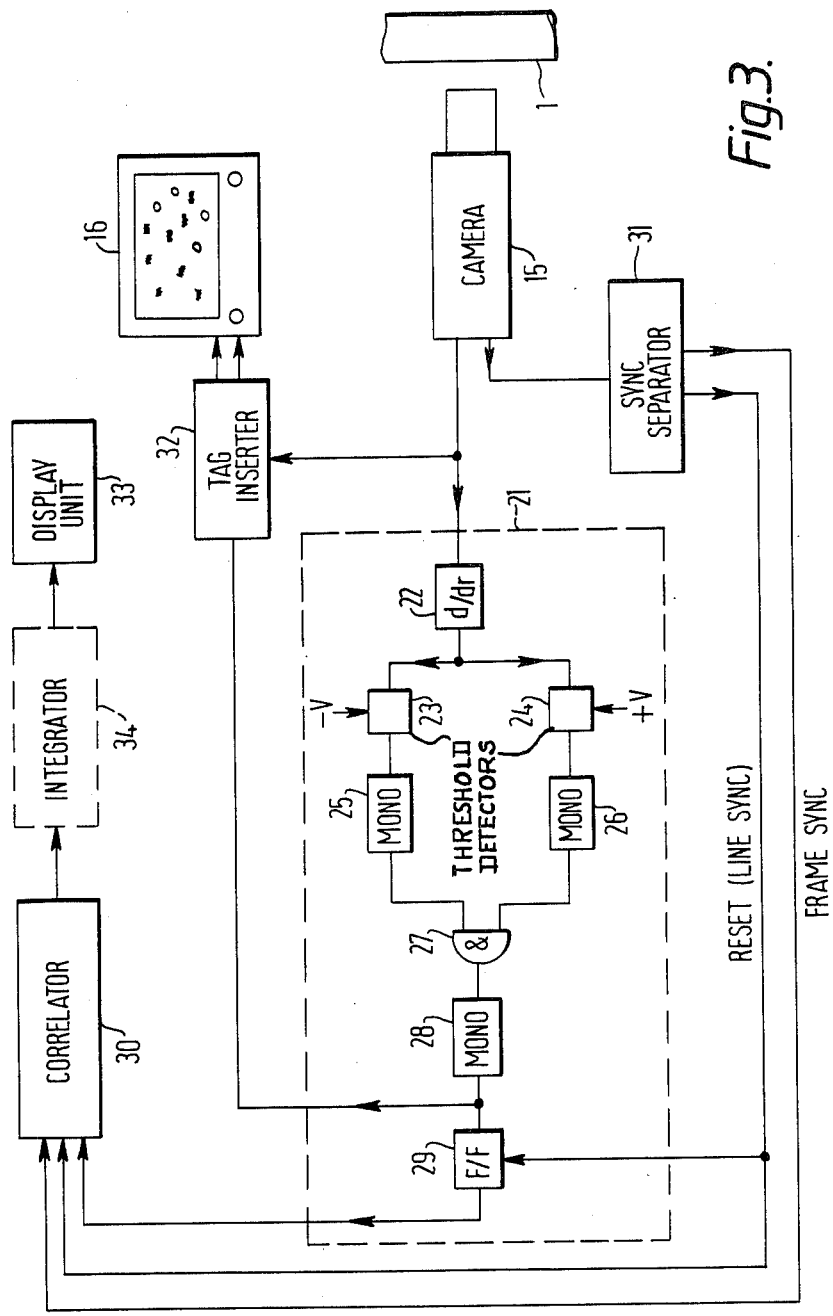
FIG. 3 is a block diagram of apparatus for measuring cell mobility within the chamber of FIGS. 1, 2.

This movement is observed and measured by the apparatus shown in FIG. 3. The chamber is observed by a linescan camera 15 e.g. a television (TV) video camera and displayed via a tag inserter 32 on a TV monitor 16. The picture image obtained is shown in FIG. 6, where cells are seen as dark spots 18 or light coloured spots 19 surrounded by a dark ring depending on which side of focus the cell is. The light spots 19 in a ring are of interest and have placed to the side a light coloured rectangular tag 20 electronically generated (detailed later) to assist in setting up the apparatus.

A cell detector 21 produces a series of logic ones and zeros representing detection of cells in an image frame in the following manner.

The TV camera 15 produces a display by raster scanning cells in the chamber 2 in a series of lines in the well known manner e.g. two fields of $312\frac{1}{2}$ lines interlaced. The direction of line scanning is perpendicular to the cell movement. Output from the camera 15 is a train of varying amplitude signals representing consecutive lines of the picture to be displayed. A total of 256 adjacent lines (out of 625) is chosen to form a single frame. As the camera 15 scans a line its vidicon output will be of two forms depending upon the type of cell scanned i.e. a dark spot (unwanted) or light spot in a dark ring (wanted). The vidicon output for part of a line is shown in FIG. 4a where a dark spot 18 is shown at (i) to have a single predominant peak and a light spot 19 in a dark ring is shown at (ii) to have a double peak. The two line signals FIG. 4a(i) and (ii) are passed through a differentiator 22 to produce signals respectively shown in FIG. 4b(i), (ii). FIG. 4b(i) has a negative peak followed by a positive peak whilst FIG. 4b(ii) has a positive peak followed by a negative peak.

Output from the differentiator 22 is split and passed through a negative threshold detector 23 and a positive threshold detector 24. The negative threshold detector 23 output triggers a monostable 25 whose output pulse (a logic one) is of short duruction. The positive threshold detector 24 output triggers a monostable 26 whose output pulse length is adjusted to be the expected time between positive and negative transitions of the line signal. Both monostables 25, 26 outputs pass to an AND gate 27 whose output triggers a monostable 28 followed by a flip flop 29. This is shown in FIG. 4d where the output of monostables 25, 26, 28 and AND gate 27 are indicated for both the signals (i) and (ii) shown in FIG. 4a, b, c.

Thus if the differentiator 22 output results in a negative threshold followed by a positive threshold detection, FIG. 4c(i), there will be no coincidence at the AND gate 27, and no signal from the monostable 28 to the flip flop 29. However when the differentiator 22 output results in a positive followed by a negative threshold detection FIG. 4c(ii) there will be coincidence at the AND gate 27 resulting in a logic one pulse from the monostable 28 to place the flip flop 29 in its logic one state. Therefore, for each line scanned, when a wanted cell appears (a light spot in a dark ring) the flip flop 29 output is a logic one irrespective of how many wanted cells there are on the line. At the end of each line signal a line synchronisation pulse from the TV camera 15 via a synchronisation separator 31 resets the flip flop 29 to zero. The synchronisation separator 31 also provides a line synchronisation pulse and a frame synchronisation pulse to the correlator 30.

Output from the flip flop 29 is thus a logic one and zero for each line in the frame image and this series of logic ones and zeros is passed into a cross correlator 30 for cross correlation with a second series of logic ones and zeros representing a later image frame.

The monostable 28 output length is arranged to be of sufficient length that when fed via a tag inserter 32 to the TV monitor 16 it produces a visible rectangular shaped light coloured tag 20. Thus each detected cell 19 is followed on the same line by a visible tag 20 and gives confirmation to an operator that the threshold levels and timing has been correctly adjusted.

The cross correlator 30 may be hard wired e.g. a delay followed by two sets of shift registers or charge coupled devices (CCD) and multipliers. Alternatively a microprocessor, e.g. an RCA COSMAC microprocessor, may be used. The microprocessor system operates on a stored program held in a "read only memory" (ROM), accepts the flip flop output data, and stores it in an ordered array in random access memory (RAM). On command from a frame synchronizing pulse 256 such data elements (representing a frame) are stored away. The microprocessor then counts a selected number of frames (determined by the operator on the basis of expected picture shift) before accepting another 128 lines of data into its RAM (256 and 128) are chosen for convenience to give $\pm 1$ TV line in 128 resolution i.e. $\simeq 2\%$ (more or less can be chosen).

Two linear arrays of data consisting of a majority of logic zeros and a few ones representing cell positions is now stored away. These two arrays are compared element for element over 128 elements, corresponding to all the elements of the second array, and the number of times a one is detected in both is accumulated by the microprocessor. The number thus formed would represent a cross-correlation co-efficient. The relative shift of the two arrays is then indexed by one element and the process repeated. This is continued until 128 assimilated numbers has been formed from 128 relative shifts.

The list of numbers is then searched to identify the largest number and the index position of this peak is noted it being the most probable picture shift from a datum of zero shift. Positive or negative shift depending on the existing potential-difference polarity. The result may be as shown in FIG. 5a and may be displayed on a display unit 33 e.g. an oscilloscope or visible display unit (VDU).

Another or a number of other pairs of frames may be processed in the same way and accumulated by an integrator 34 to improve the signal to noise ratio before the peak is sought. FIG. 5b shows the integration of 30 image frame pairs.

One picture shift determined in this way is added into a probability density function FIG. 5c of shifts stored in the microprocessor RAM until a significant number (selected by the operator) have been accumulated of the same shift, this is then output as a number of TV lines of picture shift n calculated from frames N apart and if each TV line is calibrated to represent a known distance d meter in the electrophoretic cell the velocity of picture shift and hence velocity of the cells can be calculated from $$V = \frac{nd}{20 \times 10^{-3}(N+2) + 64 \times 10^{-6}n} \, m/s$$

$20 \times 10^{-3}$ is one TV frame time and
$64 \times 10^{-6}$ is one TV line time for 50 Hz system (different for American 60 Hz system).

In a modification the flip flop is replaced by a counter which provides a digital number, representing detected cells, for each line scanned. The correlator may correlate one or a plurality of lines with a later line or number of lines.

I claim:

1. A method of measuring electrophoretic mobility of cells comprising the steps of applying an electric potential to a solution in an electrophoretic chamber, scanning a portion of the chamber in a line by line manner to provide a first image frame, processing each line of scan to provide a digital number representing detected cells in that line and to provide a first set of numbers collectively representing the first image frame, scanning and processing to provide a second set of numbers representing a second image frame a time $\tau$ later, cross correlating the two sets of numbers to determine the image movement in the time $\tau$ and hence the cell mobility of a plurality of cells in the solution.

2. Apparatus for measuring electrophoretic mobility of cells comprising an electrophoretic chamber having two spaced electrodes for applying an electric potential to a solution containing cells and separated from the electrodes by membranes, characterised by a line scan camera for producing signals representing image frames of the cells within the solution, means for processing the signal from each line of a scan from the camera to provide a digital number representing a number of detected cells in that line and a correlator for cross correlating numbers representing time spaced image frames to provide average cell mobility.

3. Apparatus as claimed in claim 2 wherein the means for processing each line of a scan from a camera indicates the presence or absence of detected cells in that line by a logic one or zero whereby at least part of an image frame is represented by a series of logic ones and zeros for correlation with a later series to indicate cell mobility.

4. Apparatus as claimed in claim 2 further comprising a tag inserter means for providing a visible mark on a television screen adjacent each cell detected.

5. Apparatus as claimed in claim 2 comprising an integrator for integrating the results of many mobility results.

6. Apparatus as claimed in claim 3 wherein the means for processing each line of a scan comprises a differentiator, two different threshold detectors, two monostables of different output pulse length having an input from the detectors and an output to an AND gate, and a flip flop set in to one state by the AND gate and reset after each line by a line synchronisation pulse from the camera.

* * * * *